(12) United States Patent
Barnes

(10) Patent No.: US 9,636,715 B1
(45) Date of Patent: May 2, 2017

(54) SANITIZING AND CLEANING PROCESS AND METHOD

(71) Applicant: Ronald L. Barnes, Owens Crossroads, AL (US)

(72) Inventor: Ronald L. Barnes, Owens Crossroads, AL (US)

( * ) Notice: Subject to any disclaimer, the term of this patent is extended or adjusted under 35 U.S.C. 154(b) by 0 days.

(21) Appl. No.: 14/798,821

(22) Filed: Jul. 14, 2015

Related U.S. Application Data

(62) Division of application No. 14/248,292, filed on Apr. 8, 2014, now Pat. No. 9,079,227.

(60) Provisional application No. 61/809,776, filed on Apr. 8, 2013.

(51) Int. Cl.
*B08B 3/00* (2006.01)
*B08B 3/02* (2006.01)
*A61L 2/18* (2006.01)

(52) U.S. Cl.
CPC .............. *B08B 3/026* (2013.01); *A61L 2/183* (2013.01); *B08B 3/02* (2013.01)

(58) Field of Classification Search
None
See application file for complete search history.

(56) References Cited

U.S. PATENT DOCUMENTS

| | | |
|---|---|---|
| 996,561 A | 6/1911 | Bradley |
| 2,721,577 A | 10/1955 | Esselman |
| 3,304,564 A | 2/1967 | Green et al. |
| 3,326,747 A | 6/1967 | Ryan et al. |
| 3,361,663 A | 1/1968 | Murray et al. |
| 3,448,045 A | 6/1969 | Hess et al. |
| 3,474,817 A | 10/1969 | Bates et al. |
| 3,563,879 A | 2/1971 | Richards et al. |
| 3,616,355 A | 10/1971 | Themy |
| 3,704,006 A | 11/1972 | Grout et al. |
| 3,925,176 A | 12/1975 | Okert |
| 3,957,949 A | 5/1976 | Senjo et al. |
| 3,964,472 A | 6/1976 | Nicollet |
| 3,977,831 A | 8/1976 | Fletcher et al. |
| 3,996,136 A | 12/1976 | Jakubek et al. |
| 4,034,965 A | 7/1977 | King |
| 4,035,296 A | 7/1977 | Armstrong |
| 4,043,913 A | 8/1977 | Hintermeister |
| 4,053,403 A | 10/1977 | Bachhofer et al. |
| 4,059,522 A | 11/1977 | Polley et al. |
| 4,111,219 A | 9/1978 | Hallberg et al. |
| 4,169,293 A | 10/1979 | Weaver |
| 4,171,256 A | 10/1979 | Themy |

(Continued)

FOREIGN PATENT DOCUMENTS

CN 202860877 U 4/2013
CN 203302204 U 11/2013

(Continued)

*Primary Examiner* — Eric Golightly
(74) *Attorney, Agent, or Firm* — Mark Clodfelter

(57) ABSTRACT

A system is proposed for cleaning and sterilization wherein a carrier fluid is provided through a spray head having a mixing chamber, the flow of carrier fluid converted to a spray by the spray head. In the mixing chamber, ozone and ozone reaction products are mixed with the flow of carrier fluid to obtain a higher mixture of ozone and ozone reaction products in the carrier fluid immediately before the carrier fluid and ozone and ozone reaction products are dispensed as a spray.

9 Claims, 3 Drawing Sheets

(56) References Cited

U.S. PATENT DOCUMENTS

| | | |
|---|---|---|
| 4,172,786 A | 10/1979 | Humphrey et al. |
| 4,201,651 A | 5/1980 | Themy |
| 4,255,257 A | 3/1981 | Greiner et al. |
| 4,283,263 A | 8/1981 | Mirabelli |
| 4,309,388 A | 1/1982 | Tenney et al. |
| 4,361,471 A | 11/1982 | Kosarek |
| 4,361,486 A | 11/1982 | Hou et al. |
| 4,372,860 A | 2/1983 | Kaas |
| 4,427,636 A | 1/1984 | Obenshain |
| 4,596,648 A | 6/1986 | Sweeney |
| 4,613,415 A | 9/1986 | Wreath et al. |
| 4,640,783 A | 2/1987 | Kern |
| 4,688,699 A | 8/1987 | Goudy, Jr. et al. |
| 4,714,092 A | 12/1987 | Sanders |
| 4,724,059 A | 2/1988 | Collier |
| 4,749,527 A | 6/1988 | Rasmusen |
| 4,761,208 A | 8/1988 | Gram et al. |
| 4,761,838 A | 8/1988 | Hargrove |
| 4,781,810 A | 11/1988 | Tucker |
| 4,797,958 A | 1/1989 | Guzzini |
| 4,804,449 A | 2/1989 | Sweeney |
| 4,804,478 A | 2/1989 | Tamir |
| 4,820,408 A | 4/1989 | Sandig |
| 4,829,607 A | 5/1989 | Huse |
| 4,959,142 A | 9/1990 | Dempo |
| 4,990,311 A | 2/1991 | Hirai et al. |
| 5,008,087 A | 4/1991 | Batchelor |
| 5,012,535 A | 5/1991 | Klotzbach |
| 5,032,292 A | 7/1991 | Conrad |
| 5,037,519 A | 8/1991 | Wiscombe |
| 5,056,168 A | 10/1991 | Mersmann |
| 5,061,343 A | 10/1991 | Azarniouch et al. |
| 5,068,040 A | 11/1991 | Jackson |
| 5,075,016 A | 12/1991 | Barnes |
| 5,082,558 A | 1/1992 | Burris |
| 5,094,734 A | 3/1992 | Torrado |
| 5,207,993 A | 5/1993 | Burris |
| 5,213,773 A | 5/1993 | Burris |
| 5,223,105 A | 6/1993 | Arthurson |
| 5,255,974 A | 10/1993 | Signer |
| 5,266,215 A | 11/1993 | Engelhard |
| 5,314,589 A | 5/1994 | Hawley |
| 5,334,383 A | 8/1994 | Morrow |
| 5,343,629 A | 9/1994 | Rae |
| D351,649 S | 10/1994 | Lin |
| 5,365,617 A | 11/1994 | Tarr |
| 5,376,265 A | 12/1994 | Szabo |
| 5,395,537 A | 3/1995 | Ellison |
| 5,433,854 A | 7/1995 | Dickerson |
| 5,451,318 A | 9/1995 | Moorehead |
| 5,474,748 A | 12/1995 | Szabo |
| 5,476,579 A | 12/1995 | Choi et al. |
| 5,536,400 A | 7/1996 | Schultz |
| 5,567,444 A | 10/1996 | Hei et al. |
| 5,572,991 A | 11/1996 | Grilliot et al. |
| 5,578,205 A | 11/1996 | Martin |
| 5,582,718 A | 12/1996 | Sobczak |
| 5,601,786 A | 2/1997 | Monagan |
| 5,622,622 A | 4/1997 | Johnson |
| 5,635,059 A | 6/1997 | Johnson |
| 5,665,228 A | 9/1997 | Leaverton et al. |
| 5,674,312 A | 10/1997 | Mazzei |
| 5,766,490 A | 6/1998 | Taylor et al. |
| 5,785,845 A | 7/1998 | Colaiano |
| 5,792,369 A | 8/1998 | Johnson |
| 5,810,043 A | 9/1998 | Grenier |
| 5,816,498 A | 10/1998 | Smith, Jr. et al. |
| 5,843,304 A | 12/1998 | Marchesseault et al. |
| 5,879,641 A | 3/1999 | Conrad et al. |
| 5,888,389 A | 3/1999 | Griffith et al. |
| 5,893,641 A | 4/1999 | Garcia |
| 5,899,641 A | 5/1999 | Pfeiffer |
| 5,904,901 A | 5/1999 | Shimono et al. |
| 5,927,338 A | 7/1999 | Boticki et al. |
| 5,935,431 A | 8/1999 | Korin |
| 5,961,920 A | 10/1999 | Soremark |
| 5,968,352 A | 10/1999 | Ditzler |
| 5,976,385 A | 11/1999 | King |
| 5,989,439 A | 11/1999 | Persinger |
| 5,997,812 A | 12/1999 | Burnham et al. |
| 6,007,726 A | 12/1999 | Yang et al. |
| 6,059,941 A | 5/2000 | Bryson et al. |
| 6,060,027 A | 5/2000 | Conrad et al. |
| 6,083,387 A | 7/2000 | LeBlanc et al. |
| 6,096,221 A | 8/2000 | Kerchouche et al. |
| 6,129,850 A | 10/2000 | Martin et al. |
| 6,132,629 A | 10/2000 | Boley |
| RE36,972 E | 11/2000 | Baker et al. |
| 6,146,524 A | 11/2000 | Story |
| 6,190,622 B1 | 2/2001 | Conrad et al. |
| 6,192,911 B1 | 2/2001 | Barnes |
| 6,207,064 B1 | 3/2001 | Gargas |
| 6,274,052 B1 | 8/2001 | Hartwig |
| 6,277,288 B1 | 8/2001 | Gargas |
| 6,279,177 B1 | 8/2001 | Gloodt |
| 6,280,615 B1 | 8/2001 | Phillips et al. |
| 6,332,981 B1 | 12/2001 | Loyd |
| 6,340,736 B1 | 1/2002 | Coenen et al. |
| 6,342,154 B2 | 1/2002 | Barnes |
| 6,357,060 B2 | 3/2002 | Gloodt |
| 6,358,425 B1 | 3/2002 | King |
| 6,368,472 B1 | 4/2002 | McGuire |
| 6,405,387 B1 | 6/2002 | Barnes |
| 6,426,053 B1 | 7/2002 | Barnes |
| 6,458,257 B1 | 10/2002 | Andrews et al. |
| 6,464,868 B1 | 10/2002 | Korin |
| 6,491,811 B2 | 12/2002 | Conrad et al. |
| 6,491,879 B2 | 12/2002 | Conrad |
| 6,497,840 B1 | 12/2002 | Palestro et al. |
| 6,503,402 B2 | 1/2003 | Jensen |
| 6,517,713 B2 | 2/2003 | Gargas |
| 6,523,192 B1 | 2/2003 | Gloodt |
| 6,537,494 B2 | 3/2003 | Garlick |
| 6,551,518 B2 | 4/2003 | Gargas |
| 6,551,519 B1 | 4/2003 | Hartwig |
| 6,589,489 B2 | 7/2003 | Morrow et al. |
| 6,620,379 B1 | 9/2003 | Piuk et al. |
| 6,623,635 B2 | 9/2003 | Barnes |
| 6,627,053 B2 | 9/2003 | Hirota et al. |
| 6,630,105 B1 | 10/2003 | O'Neill et al. |
| 6,680,026 B1 | 1/2004 | Denkewicz, Jr. et al. |
| 6,692,645 B1 | 2/2004 | Gargas |
| 6,723,233 B1 | 4/2004 | Barnes |
| 6,814,877 B2 | 11/2004 | Gargas |
| 6,881,331 B1 | 4/2005 | Barnes |
| 6,893,610 B1 | 5/2005 | Barnes |
| 6,951,633 B1 | 10/2005 | Barnes |
| 6,967,008 B1 | 11/2005 | Barnes |
| 6,974,562 B2 | 12/2005 | Ciampi et al. |
| 6,984,295 B2 | 1/2006 | Shiue et al. |
| 7,008,529 B2 | 3/2006 | Nakanishi et al. |
| 7,060,180 B1 * | 6/2006 | Barnes ................ A61H 33/14 210/167.11 |
| 7,086,407 B2 | 8/2006 | Lynn |
| 7,135,099 B2 | 11/2006 | Kondo et al. |
| 7,135,108 B1 | 11/2006 | Barnes |
| 7,186,334 B1 | 3/2007 | Barnes |
| 7,329,343 B1 * | 2/2008 | Barnes .................. C02F 1/78 204/660 |
| 7,335,291 B2 | 2/2008 | Kondo et al. |
| 7,604,735 B1 | 10/2009 | Barnes |
| 7,604,780 B2 | 10/2009 | Teran et al. |
| 7,658,891 B1 | 2/2010 | Barnes |
| 7,695,606 B2 | 4/2010 | Tholen |
| 7,780,909 B2 | 8/2010 | Sparks |
| 7,794,608 B2 | 9/2010 | Denkewicz, Jr. et al. |
| 7,838,951 B2 | 11/2010 | Kimino |
| 7,875,173 B1 | 1/2011 | Barnes |
| 7,883,622 B1 | 2/2011 | Barnes |
| 7,993,600 B2 | 8/2011 | Doyle et al. |
| 8,048,370 B1 | 11/2011 | Barnes |
| 8,075,784 B1 | 12/2011 | Barnes |
| 8,409,434 B2 | 4/2013 | Andrews et al. |
| 8,414,839 B1 | 4/2013 | Barnes |

(56) References Cited

U.S. PATENT DOCUMENTS

| | | |
|---|---|---|
| 8,491,775 B1 | 7/2013 | Barnes |
| 9,079,227 B2 | 7/2015 | Barnes |
| 2002/0023866 A1 | 2/2002 | Barnes |
| 2004/0096354 A1 | 5/2004 | Nomura |
| 2011/0085934 A1 | 4/2011 | Joshi |

FOREIGN PATENT DOCUMENTS

| | | | |
|---|---|---|---|
| EP | 0269941 A1 | | 6/1988 |
| ES | 19880003522 | 1118 | 2/1990 |
| JP | 356045806 A | | 4/1981 |
| JP | 62176594 A | | 8/1987 |
| JP | 0318390 A | | 8/1991 |
| JP | 04156994 A | | 5/1992 |
| JP | 05-071861 A | | 3/1993 |
| JP | 09172959 A | | 7/1997 |
| JP | 09239368 A | | 9/1997 |
| JP | 10174983 B2 | | 6/1998 |
| JP | 11192487 A | | 7/1999 |
| JP | 11206316 A | | 8/1999 |
| JP | 3158163 B2 | | 2/2001 |
| JP | 2006334552 A | | 12/2006 |
| SU | 1798317 A1 | | 3/1993 |
| WO | 2013181469 A1 | | 5/2013 |
| WO | 2013181469 A1 | | 12/2013 |

\* cited by examiner

SANITIZING AND CLEANING PROCESS AND METHOD

CROSS REFERENCE TO RELATED APPLICATIONS

This application is a divisional application of Applicant's U.S. patent application Ser. No. 14/248,292, filed Apr. 8, 2014, and issued as U.S. Pat. No. 9,079,227 on Jul. 14, 2015, which claims the benefit of Applicant's U.S. provisional application No. 61/809,776, filed April 2008 12013.

FIELD OF THE INVENTION

This application relates generally to spay heads, and particularly to a spray head that mixes ozone in a combination of mist and vapors that may contain cleaning compounds.

BACKGROUND OF THE INVENTION

Spray systems for dispensing cleaning solutions are well-known, and range from small, handheld bottles having a trigger-operated pump and spray nozzle to pressure washers that can develop thousands of pounds of pressure, and which can dispense a cleaning solution along with pressurized water. For handheld spray bottles, a dilute cleaning solution containing soaps, surfactants, bleaches and the like is contained within the bottle, and a trigger connected to a pump is operated to dispense the solution as a spray or stream. Larger systems, such as a pressure washer, are connected to a separate source of water, and pressurize the water to, in most cases, over 1,000 PSI. A separate container of a concentrated cleaning solution is provided, and which is metered into the high-pressure stream of water. In other systems, steam cleaners and/or pressure washers are used in butcher shops in conjunction with steam, soap solutions, disinfectant solutions and rinses to clean and sanitize surfaces contacted by meat.

Cruise ships in particular have problems with spread of various diseases among passengers due to crowded conditions, and the preparation ol4-6 meals a day. In particular, Norovirus and *e. Coli* can infect hundreds of people even on a relatively short cruise. While passengers and crew are instructed in health and cleanliness matters and these ships are thoroughly cleaned after each cruise, problems still persist.

Ozone is one of the most effective sanitizers known, and is more effective than chlorine as a disinfectant. It is also one of the safest and most convenient to use, because ozone breaks down into oxygen and leaves no harmful residues. However, its lifespan as a sanitizer is short due to its high reactive potential. Further, the byproducts of ozone, such as peroxides, free radicals and others, collectively known as "ozonites", are also high in reactive potential and useful for cleaning and sterilizing. As such, ozone must be generated and used immediately.

In view of the foregoing, Applicant proposes to combine or modify various sanitizing systems for use with ozone, for more effective cleaning and disinfection.

DETAILED DESCRIPTION OF THE DRAWINGS

A cleaning system including at least ozone and a cleaning solution or solvent is disclosed. A spray head is provided that can be configured or fabricated to fit many cleaning implements, such as pressure washers, hand held, manually operated pumps, or spray heads can be built into cleaning machines such as dishwashers. In some embodiments, the ozone generator that creates ozone for the spray head may be used in conjunction with a halogen salt generator that also mixes a halogen, such as chlorine, bromine or even iodine, to the solution from the spray head. In other embodiments, reaction products from the chlorine generation process, such as NaOH, hydroxyl radicals, peroxides, a halogen salt, oxygen, and others, may also be mixed into the cleaning solution by the spray head, or mixed into the cleaning solution prior to being sprayed by the spray head. In yet other embodiments, ozone, chlorine and reaction products may be combined with a conventional cleaning soap or other cleaning compounds. In some embodiments, a spray nozzle may be configured to dispense steam, as from a steam cleaner, with any or all of ozone, a halogen such as chlorine and reaction products from generating chlorine from a chlorine generator inserted into the steam from the spray nozzle.

Figure 1:
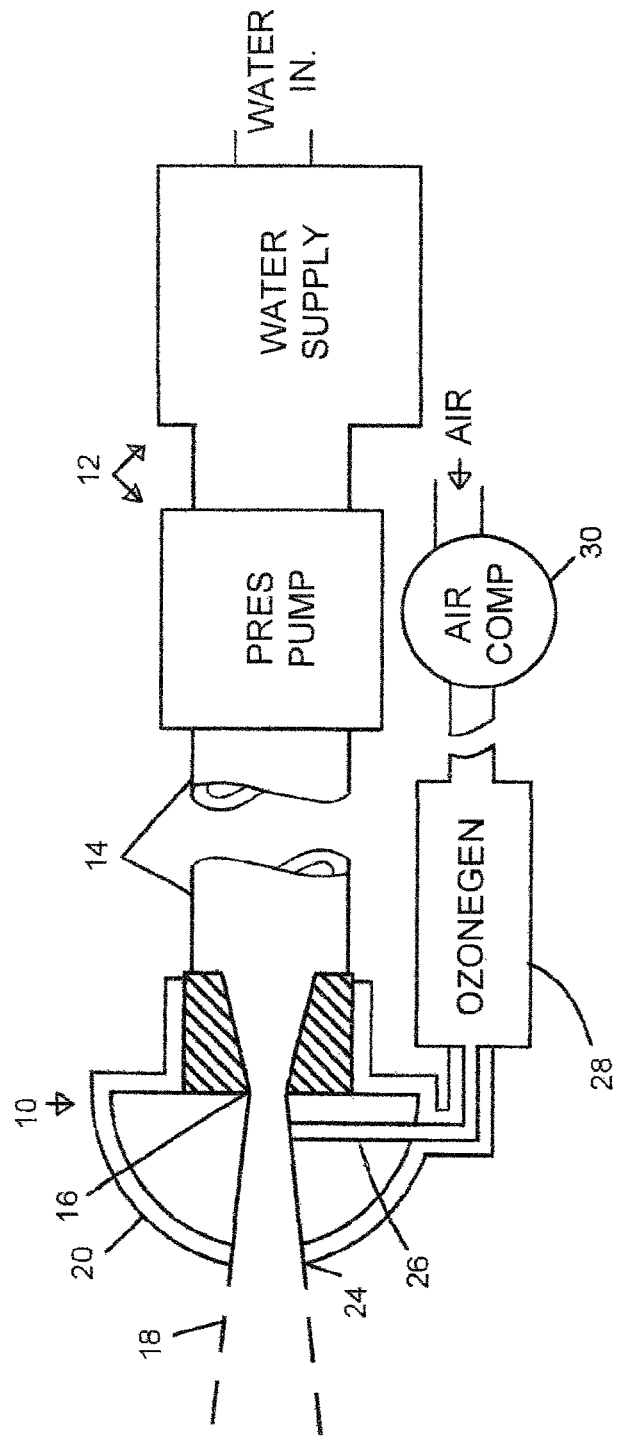
FIG. 1 is a diagrammatic view of a disinfection and cleaning system of the invention.

Referring to FIG. 1, a simplest embodiment is shown. Here, a spray nozzle 10 may be fitted to a pressure washer, a dishwasher or the like, or a hose similar to a garden hose and connected to a pressurized source of water, a steam cleaner or even a hand-held spray bottle manually operated by a trigger, all these devices illustrated graphically by water supply and pump 12, and which is configured so that a carrier fluid, such as pressurized water, steam or a cleaning solution, is passed through a tube 14 that leads to nozzle 10. Nozzle 10 is configured having an outlet or orifice 16 through which the water or cleaning solution 18 is forced in a stream or spray, which may be a high-pressure stream, or which may be a lower pressure stream, or a spray for wider area coverage and sanitization. A chamber or plenum 20 generally surrounds outlet or orifice 16, which is tapered as shown on its inner side in order to speed up the flow in a similar manner as a Venturi. This causes the stream to expand after it passes from orifice 16, and also develops a suction within chamber or plenum 20. The expanded stream passes from chamber or plenum 20 through an opening 24; which is typically larger than orifice 16, and may have different configurations. For instance, opening 24 may be configured as a slot in order to develop a fan-shaped spray, or may be round to develop a collimated stream or spray.

The open end of a tube or the like 26 is positioned near orifice 16 so that the suction developed by the stream issuing from internally tapered orifice 16 is felt at the open end of tube 26, and which draws at least ozone from ozone generator 28 into stream 18 just prior to the stream issuing from the spray nozzle. As such, the ozone is generated and mixed in stream 18 immediately as the stream is passed from nozzle 10. This appears to be one of the most effective ways to use ozone by itself as a sanitizer in the instant invention. As noted in Applicant's incorporated PCT application no. PCT/US2013/043485 as originally filed at pg. 7 lines 17-20, an ozone generator may be configured to inject ozone into water flowing through the ozone generator and almost instantly expose the water to intense ultraviolet light, creating opportunity for advanced oxidation and other reactions. As noted at pg. 11 lines 12-21 of the referenced PCT application is a description of how the 255 nm wavelength 11 ultraviolet lamp breaks down ozone in the presence of water or water vapor to form hydroxyl radicals, which are very effective as a sanitizer. A compressor 30 may be used to force air through ozone generator 30 into chamber 20 for positive control over the flow of air and ozone. In some embodiments, the compressor may be used as a regulator to limit airflow through the ozone generator in order to develop higher concentrations of ozone.

Ozone generator 28 may be an ultraviolet ozone producing lamp, a corona discharge device or any other ozone-producing device. For example, one ozone generator might be an ozone generator as described in Applicant's PCT application no. PCT/US2013/043485, filed 30 May 2013, which is incorporated in its entirety herein by reference, and which may also be configured to provide a flow of irradiated and sterilized water as water supply 12. In any case, ozone generator 28 provides ozone via tube 26 to a point within plenum 20 immediately adjacent stream 18 where Venturi suction is strongest. Typically, anti-backflow valves (not shown) are provided in tube 26 so that water cannot flow back into the ozone generator. As noted, in some embodiments, an air compressor 30 may be provided to actively pump oxygen or air through ozone generator 28, while in other embodiments oxygen or air may be drawn through ozone generator 28 by Venturi action developed by the end of tube 26 being in or closely proximate to stream 18. In yet other embodiments, air or oxygen may be provided to the ozone generator and subsequently to tube 26 from a pressurized container, a pressure swing oxygen concentrator or other similar device. As noted, spray head 20 may be any spray head, such as a pressure washer, spray heads in dishwashers, a manually operated spray bottle, or any other application where ozone is needed in a stream or spray of water 18. As such, a stream of water containing ozone may be used as an effective rinsing and sanitizing solution, such as on a cruse ship or in a rinse procedure during cleaning of a butcher shop or the like.

Figure 2:
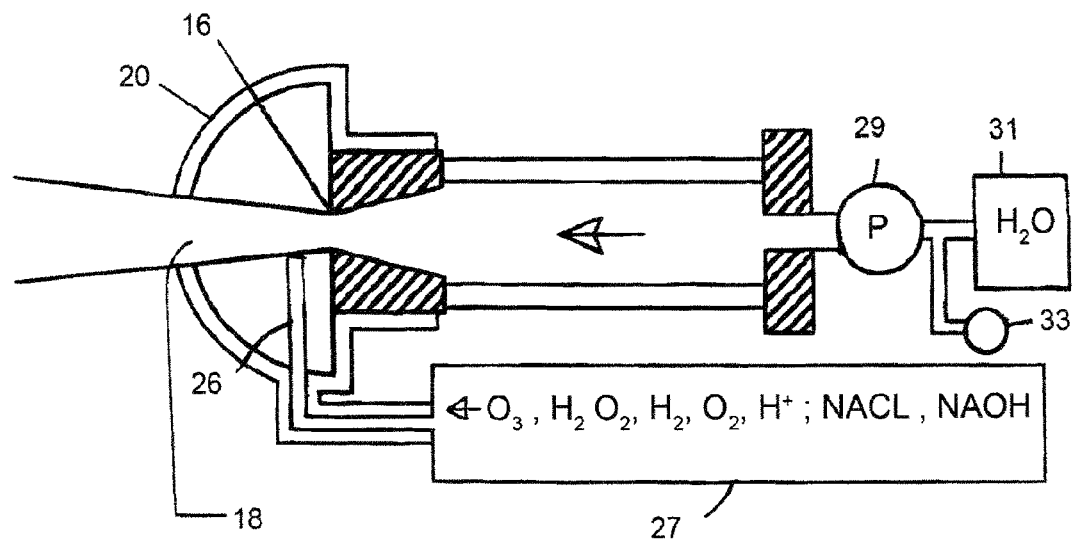
FIG. 2 is a partially cut-away, partially diagrammatic view of a cleaning and disinfection system of the invention.

In other embodiments, and referring to FIG. 2, a spray head 20 as described above including chamber 20 and tube 26 is connected to one or more of a source 27 of ozone, hydrogen peroxide, oxygen, hydroxyl radicals, a salt, sodium hydroxide, potassium hydroxide, silver, zinc, tin and copper compounds or any other beneficial compound or element, and which may be in addition to soap or another cleaning compound. In this embodiment, the compounds and elemental ions of source 27 would be dissolved in water, and drawn by Venturi action into stream 18. A pump 29 or source of pressurized water drives water through orifice 16 to develop spray 18. In some embodiments, source 31 may be independent of a residential supply, such as where the apparatus is portable, as by being configured as a cart, hand-carried or configured as a backpack-type device. In some embodiments, at least some of the substances may be provided prior to pump 29 in order to promote mixing of the substances by the pump.

Figure 3:
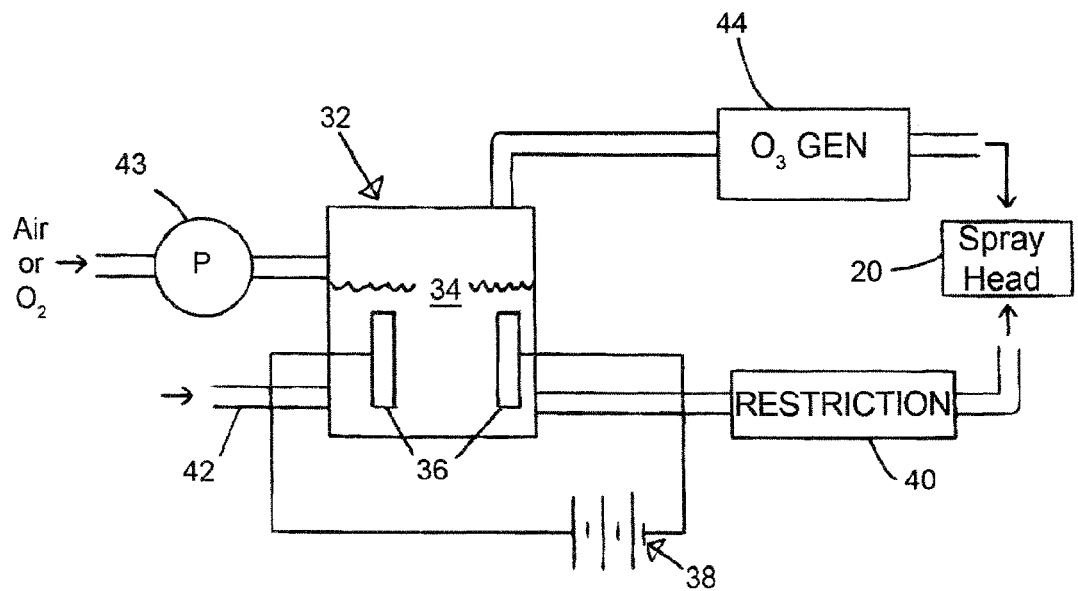
FIG. 3 is a block diagram of another embodiment of the invention.

As shown in FIG. 3, at least some of such substances may be provided by a halogen salt generator 32 containing a halogen salt solution 34. A pair of electrolysis plates 36 are provided, the plates having a sufficient voltage potential applied to them, as by a DC power source 38, so as to electrolyze the halogen salt and release a sanitizing halogen, such as chlorine, bromine or iodine. In some embodiments the halogen salt supply 34 remains relatively constant until depleted, whereupon the supply is changed, while in other embodiments a flow of the halogen salt solution and reaction products is applied to spray head 20 via a restriction 40. Restriction 40 limits the quantity of fluid from supply 34 that is allowed to flow to spray head 20. In some embodiments, the flow may be controlled at an inlet 42 at a predetermined rate, as by a manually set valve, or an automatically set valve responsive to a liquid level sensor, a flow rate sensor or other sensor for sensing quantity of fluid in ozone generator 32. In other embodiments, the fluid in halogen generator 32 may be drawn through the halogen generator by Venturi action developed by spray head 20. In addition, a residual of halogen that escapes from halogen supply 34 is applied along with air or oxygen through ozone generator 44, and subsequently to spray head 20. In some embodiments, an air pump 43 may be provided either to boost the supply of air or to regulate the air flow as noted above. In some embodiments, a flow of the halogen salt solution may be recirculated between a reservoir and the halogen salt generator and ozone generator in order to build up levels of ozone and the released halogen in the reservoir prior to providing the salt solution containing halogen and reaction products and the gaseous mixture containing air, ozone and the halogen to spray head 20. Advantages of the embodiments of FIGS. 2 and 3 are that many reactions occur that facilitate cleaning and sanitizing functions. Ozone, hydroxyl radicals, hydrogen peroxide, halogen sanitizers and hydroxides are provided to the spray or stream from opening 18 as it is emitted. By doing this, much more of the reactivity of the ozone, halogen and other chemicals is retained. In contrast, other systems that insert the ozone and other chemicals upstream from the sprayer head cause much of the reactivity of such chemicals to be lost because of rapid reaction times of these chemicals.

In another embodiment the water is heated to provide hot water, steam or hot vapor. An acid and redox controller can be added for electrolysis chamber 34 (FIG. 3) to control pH and ORP (oxidation reduction potential), with a controller cycling the chemical/ozone feed and supplying acid to electrolysis chamber 34. One or more metallic ionic additives, such as Silver, zinc, tin and copper, may be added to chamber 34 to provide a residual sanitizer to the spray.

Figure 4:
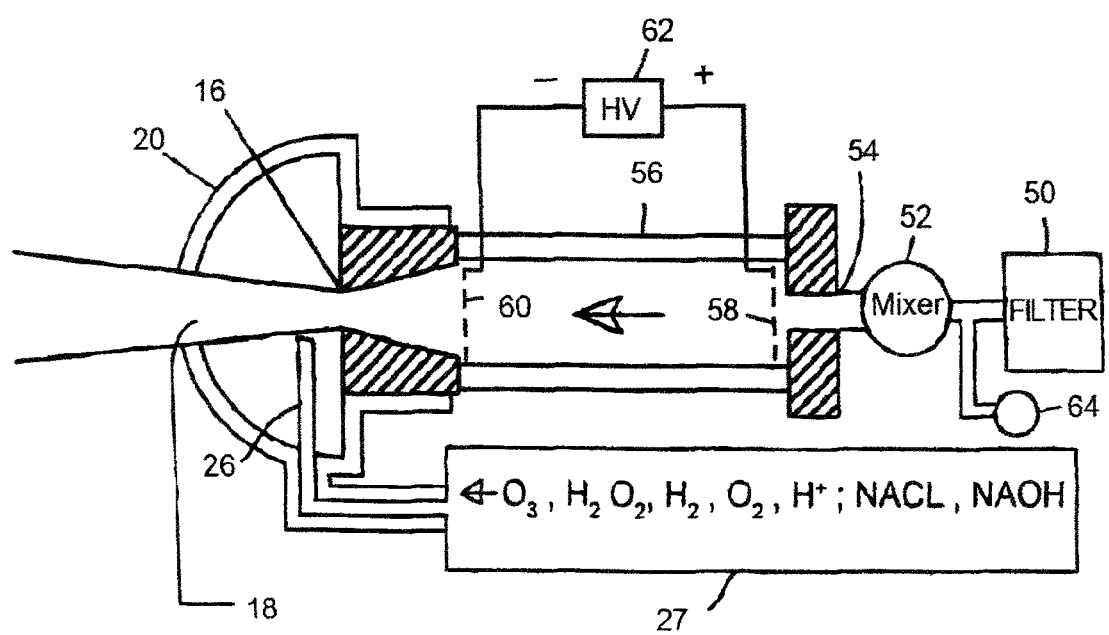
FIG. 4 is a block diagram of an electrostatic embodiment of the invention.

FIG. 4 illustrates an embodiment that uses electrostatic potentials to accelerate ionized components in a flow of water. Here, pressurized water is provided via a filter 50 to a mixer 52, and subsequently to an orifice 54. Orifice 54 is configured to provide a relatively fine spray of water to the interior of a chamber 56. A first screen, grid, mesh or the like 58 is provided within chamber 56 adjacent orifice 54, and a second screen, grid or the like 60 is provided as shown adjacent orifice 16. A high voltage source 62 provides a high voltage of 3000 volts or more and is connected as shown, with a positive potential applied to screen 58 and a negative potential applied to screen 60. A source of ionizable material, such as manganese, sodium, potassium or the like is applied to the flow of water from source 64 so that ions may be developed. In use, the electrostatic potential applied to screen 58 ionizes the ionizable material and creates ions in the spray of water from orifice 54. The ions are then accelerated by the potential on screen 60, pulling the spray out orifice 16 in a combination of a fine mist and vapor that is applied to surface to be sterilized, or to air in a room to be sterilized. As noted above, ozone and other substances are applied to the stream via tube 26. One possible advantage to this particular system is that the mist or vapor, being negatively charged, is attracted to and adheres to various surfaces. It is noted that the solids in the mist emitted at orifice 16 are in a very small quantity in order to not fog the air or create breathing problems, or create a dust on furniture.

It should be apparent that the components of my invention may be combined or assembled in any useful way, and that any of the mentioned compounds may be used separately or together, in any combination deemed to be useful for cleaning and sterilizing purposes.

Having thus described my invention and the manner of its use, it should be apparent to those of average skill in the relevant arts that incidental changes may be made thereto that fairly fall within the scope of the following appended claims, wherein

I claim:

1. A process for sanitizing and cleaning comprising:

providing a flow of carrier fluid, providing a spray head having a mixing chamber that receives said flow of carrier fluid, said spray head converting said carrier fluid to a spray and dispensing said spray, in said mixing chamber, mixing at least ozone and ozone reaction products with said carrier fluid, whereby said ozone and ozone reaction products are provided in said spray by mixing said ozone and ozone reaction products in said carrier fluid immediately before said carrier fluid containing said ozone and ozone reaction products is dispensed as said spray.

2. A process as set forth in claim 1 further comprising providing said ozone and ozone reaction products into said mixing chamber via a passageway having an opening where said carrier fluid enters said mixing chamber.

3. A process for sanitizing and cleaning as set forth in claim 1 further comprising providing a halogen to said carrier.

4. A process for sanitizing and cleaning as set forth in claim 3 wherein said providing a halogen to said carrier fluid further comprises providing chlorine to said carrier fluid.

5. A process as set forth in claim 2 wherein said mixing at least ozone and ozone reaction products further comprises mixing at least hydroxyl ions with said carrier fluid.

6. A process as set forth in claim 5 further comprising creating said hydroxyl ions in an ozone generator coupled to said spray head.

7. A process as set forth in claim 6 wherein said creating hydroxyl ions further comprises creating a large quantity of hydroxyl ions and almost no said ozone, so that said spray from said spray head contains almost no said ozone but promotes advanced oxidation in said spray.

8. A process as set forth in claim 1 further comprising using an air pump to pump air through an ozone generator, for producing said ozone and ozone reaction products and supplying said ozone and ozone reaction products to said mixing chamber.

9. A process as set forth in claim 8 wherein said producing ozone and ozone reaction products further comprises producing more said ozone reaction products than said ozone, for promoting advanced oxidation in said spray.

* * * * *